United States Patent
Shanbhag et al.

(10) Patent No.: US 11,377,410 B2
(45) Date of Patent: Jul. 5, 2022

(54) PROCESS FOR GENERATING A MIXED MULTICOMPONENT VAPOR FOR PREPARATION OF MONOALKYL ETHERS OF DIPHENOLS

(71) Applicant: CAMLIN FINE SCIENCES LIMITED, Mumbai (IN)

(72) Inventors: Anil Purushottam Shanbhag, Mumbai (IN); Arjun Sudhakar Dukane, Mumbai (IN)

(73) Assignee: CAMLIN FINE SCIENCES LIMITED, Mumbai (IN)

( * ) Notice: Subject to any disclaimer, the term of this patent is extended or adjusted under 35 U.S.C. 154(b) by 0 days.

(21) Appl. No.: 15/313,076

(22) PCT Filed: May 19, 2015

(86) PCT No.: PCT/IN2015/050037
§ 371 (c)(1),
(2) Date: Nov. 21, 2016

(87) PCT Pub. No.: WO2015/177813
PCT Pub. Date: Nov. 26, 2015

(65) Prior Publication Data
US 2017/0158589 A1    Jun. 8, 2017

(30) Foreign Application Priority Data
May 21, 2014    (IN) .......................... 1702/MUM/2014

(51) Int. Cl.
*C07C 41/09*        (2006.01)
*B01J 37/03*        (2006.01)
(Continued)

(52) U.S. Cl.
CPC .............. *C07C 41/09* (2013.01); *B01J 8/067* (2013.01); *B01J 27/16* (2013.01); *B01J 35/023* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| RE33,007 E * | 8/1989 | Bier ..................... | B01D 3/06 203/12 |
| 5,189,225 A | 2/1993 | Furusaki et al. | |

(Continued)

FOREIGN PATENT DOCUMENTS

| | | |
|---|---|---|
| EP | 0509927 A1 | 10/1992 |
| EP | 0914854 A2 | 5/1999 |

(Continued)

OTHER PUBLICATIONS

International Search Report, dated Dec. 15, 2015 for corresponding International Application No. PCT/IN2015/050037.
(Continued)

*Primary Examiner* — Rosalynd A Keys
(74) *Attorney, Agent, or Firm* — Maschoff Brennan

(57) ABSTRACT

This invention comprises a process and a system thereof comprising apparatuses for developing multi-component vapor mixture by heating of solution of reactants comprising one or more of diphenols, or diphenol derivatives, and an organic compound, wherein the organic compound is one which upon reacting in a vapor state in presence of a catalyst with diphenols, or diphenol derivatives, produces a monoalkyl ether of a dihydric phenolic compound; and wherein the entire solution of reactants completely transforms into a super-heated multi-component vapor using heaters without
(Continued)

the use of thin film evaporator. The complete transformation of the entire solution of said reactants in to super-heated multicomponent vapor is achieved by heating the entire solution firstly by a pre-heater followed by further heating by a super-heater, further comprising removal of the condensed high boilers and tar to drain, and subjecting the superheated vapor to vapor phase reaction mediated by catalyst to get monoalkyl ether of a dihydric phenolic compound.

8 Claims, 1 Drawing Sheet

(51) Int. Cl.
| | | |
|---|---|---|
| *B01J 37/08* | (2006.01) | |
| *B01J 27/16* | (2006.01) | |
| *B01J 37/00* | (2006.01) | |
| *B01J 8/06* | (2006.01) | |
| *B01J 35/02* | (2006.01) | |
| *B01J 35/10* | (2006.01) | |
| *B01J 37/02* | (2006.01) | |
| *B01J 37/04* | (2006.01) | |

(52) U.S. Cl.
CPC ......... *B01J 35/026* (2013.01); *B01J 35/1014* (2013.01); *B01J 37/009* (2013.01); *B01J 37/0009* (2013.01); *B01J 37/0063* (2013.01); *B01J 37/0236* (2013.01); *B01J 37/031* (2013.01); *B01J 37/04* (2013.01); *B01J 37/08* (2013.01); *B01J 2208/0053* (2013.01); *B01J 2208/00221* (2013.01); *B01J 2208/00256* (2013.01)

(56) References Cited

U.S. PATENT DOCUMENTS

| | | |
|---|---|---|
| 5,248,835 A | 9/1993 | Shiomi et al. |
| 6,512,147 B2 * | 1/2003 | Inaba .................. B01D 1/0094 568/650 |

FOREIGN PATENT DOCUMENTS

| | | |
|---|---|---|
| EP | 1080766 A1 | 3/2001 |
| WO | WO 01/74485 A1 | 3/2001 |

OTHER PUBLICATIONS

Written Opinion of the ISA, dated Dec. 15, 2015 for corresponding International Application No. PCT/IN2015/050037.
Reinhard Billet, Ullmann'S Encyclopedia of industrial chemistry, "Evaporation", Jun. 15, 2000, pp. 1-36 (36 pages).
Extended European Search Report, dated Jan. 17, 2018, for corresponding European application No. 15 795 324.1 (9 pages).
First China Office Action, dated Aug. 28, 2018, for corresponding China application No. 201580026157.4 with English translation (17 pages).
Second China Office Action, dated Apr. 25, 2019, for corresponding China application No. 201580026157.4 with English translation (10 pages).
European Office Action, dated May 13, 2019 for corresponding European application No. 15 795 324.1 (7 pages).
India First Examination Report, dated Jul. 18, 2019 for corresponding India application No. 1702/MUM/2014 (6 pages).
China Decision of Rejection, dated Jan. 15, 2020 for corresponding China application No. 201580026157.4 with English translation (11 pages).

* cited by examiner

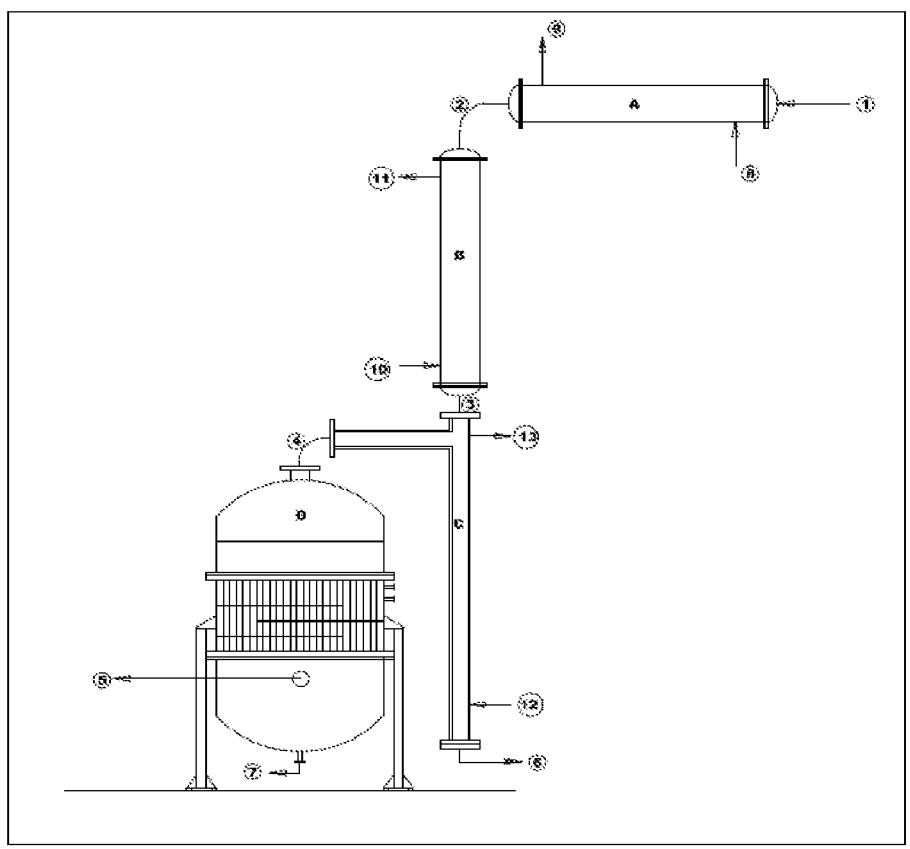

PROCESS FOR GENERATING A MIXED MULTICOMPONENT VAPOR FOR PREPARATION OF MONOALKYL ETHERS OF DIPHENOLS

FIELD OF INVENTION

This invention pertains to monoalkyl ethers of diphenols. More particularly it pertains to a process for preparation of monoalkyl ethers of diphenols. Still more particularly it pertains to generating a mixed multi-component vapor for preparation of monoalkyl ethers of diphenols.

BACKGROUND OF THE INVENTION

One method of preparation of monoalkyl ethers of diphenols comprises reacting a diphenol or a diphenol derivative such as Catechol, Hydroquinone, Resorcinol, 4-Methyl catechol, 4-Chloro catechol etc. with aliphatic and alicyclic alcohols such as Methanol, ethanol, Isopropyl alcohol, Isobutyl alcohol, tert-butyl alcohol, cyclohexanol etc. in vapor/gas state in presence of a phosphorus-containing catalyst. In this method, achieving a mixed vapor phase of the two reactants in proper proportion is a challenging task because the diphenol or a diphenol derivatives have higher boiling point whereas aliphatic and alicyclic alcohols have comparatively lower boiling point. Hence, evaporating a solution of the diphenol or a diphenol derivatives with aliphatic and alicyclic alcohols in conventionally known methods invariably results in higher proportion of aliphatic and alicyclic alcohols in the resulting two-component vapor mixture. Further, if both these components are vaporized independently and then vapors mixed together prior to exposure to catalytic bed, it has been seen that significant degradation of the diphenol or a diphenol derivative occurs.

To achieve efficient conversion of the solution of diphenol or a diphenol derivative and aliphatic and alicyclic alcohols, EP0914854 has disclosed an apparatus for generating a mixed multi-component vapor, comprising a thin film evaporator (1) having a feed inlet (1a) through which a mixed multi-component liquid comprising two or more liquid components different in boiling temperature from each other and soluble in or compatible with each other is fed into the evaporator and a delivery outlet (1b) through which a resultant mixed multi-component vapor is delivered from the evaporator; a feed line (2) for feeding the mixed multi-component liquid, connected to the feed inlet of the evaporator; a delivery line (5) for delivering the resultant mixed multi-component vapor, connected to the delivery outlet of the evaporator; and a forcedly liquid-circulating line (3) having a circulation inlet end (3a) connected to a delivery end side portion of the evaporator, a circulation outlet end (3b) connected to a feed side end portion of the evaporator and a liquid transporting means (4) arranged between the circulation inlet end and the circulation outlet end of the circulating line, whereby a non-evaporated portion of the mixed multi-component liquid is forcedly circulated through the circulation inlet end, the liquid transporting means and the circulation outlet end of the circulating line.

EP0914854 has also disclosed a process for generating a mixed multi-component vapor comprising the steps of: feeding a mixed multi-component liquid comprising two or more liquid components different in boiling temperature from each other and soluble in or compatible with each other into a feed side end portion of a thin film evaporator; evaporating the mixed multi-component liquid in the evaporator; and delivering a resultant mixed multi-component vapor from a delivery side end portion of the evaporator, wherein a non-evaporated portion of the mixed multi-component liquid present in the evaporator is forcedly circulated through a circulating line having a circulation inlet end connected to the delivery side end portion of the evaporator, a circulation outlet end connected to the feed side end portion of the evaporator, and forcedly liquid-transporting means located between the circulation inlet end and the circulation outlet end of the circulating line, by withdrawing the non-evaporated portion of the mixed multi-component liquid from the delivery side end portion of the evaporator through the circulation inlet end and returning the withdrawn non-evaporated portion of the mixed multi-component liquid into the feed side end portion of the evaporator through the forcedly liquid-transporting means and the circulation outlet end of the circulating line, thereby to promote the simultaneous evaporation of the two or more liquid components and the generation of a mixed multi-component vapor in which the two or more components are present in substantially the same composition as that of the mixed multi-component liquid.

However, this process and apparatus are capital intensive and inconvenient to operate. A simpler process involving simple equipment/apparatus was needed.

SUMMARY OF THE INVENTION

This invention comprises a process for developing multi-component vapor mixture by heating of solution of reactants comprising one or more of diphenols, or diphenol derivatives, and an organic compound, wherein the organic compound is one which upon reacting in a vapor state in presence of a catalyst with diphenols, or diphenol derivatives, produces a monoalkyl ether of a dihydric phenolic compound; and wherein the entire solution of reactants completely transforms into a super-heated multi-component vapor using heaters without the use of thin film evaporator. The complete transformation of the entire solution of reactants in to super-heated multicomponent vapor is achieved by heating the entire solution firstly by a pre-heater followed by further heating by a super-heater. The process further comprises steps of: (a) removal of the condensed high boilers and tar to drain, and (b) subjecting the superheated vapor to vapor phase reaction mediated by catalyst to get monoalkyl ether of a dihydric phenolic compound. The process further comprises achieving removal of the condensed high boilers is in a jacketed vessel which is kept heated by hot oil circulating through the jacket and the super-heated is subjected to vapor phase catalytic reaction mediated in a vapor phase catalytic reactor containing an Aluminium/Phosphorus catalyst.

This invention also comprises a system for developing multi-component vapor mixture by heating of solution of reactants comprising one or more of diphenols, or diphenol derivatives, and an organic compound, wherein the organic compound is one which upon reacting in a vapor state in presence of a catalyst with diphenols, or diphenol derivatives, produces a monoalkyl ether of a dihydric phenolic compound; wherein the entire solution of reactants completely transforms into a super-heated multi-component vapor using heaters without the use of thin film evaporator, the system of claim 9 comprising: a stainless steel reactor under a nitrogen atmosphere for making a solution of a diphenol or a diphenol derivative in the organic compound at room temperature and heating the same to about 50-50-70° C., a pre-heater to heat the solution to get vapors and a super-heater to heat the vapors to get super-heated vapors multicomponent mixture from the said solution, a jacketed section/vessel (C) for receiving superheated steam at its top and allowing the same from the top end to pass to the vapor phase catalytic reactor (D) and facilitating separation of condensed high boilers and tar that comes out of super-heater with superheated vapors to flow down its length over the inner surface of the jacketed section which is heated by hot oil to a temperature that shall re-evaporate the condensed high boilers, and allowing negligible quantity of high boilers which do not re-evaporate and tars that are formed to be drained out from the outlet at the bottom end (8), The system of this invention further comprises multiplicity of tubular reactors arranged in the vapor phase catalytic reactor (D), the tubular reactors being packed with heterogeneous Aluminum/Phosphorus catalyst capable of catalyzing a reaction in vapor state between the diphenol/diphenol-derivative and the organic compound in vapor phase to produce a monoalkyl ether of a dihydric phenolic compound to produce a monoalkyl ether of a dihydric phenolic compound in the tubular reactors upon heating to 240-300° C. by circulating hot oil & kept under Nitrogen atmosphere throughout the course of the reaction to achieve the above said reaction, a receiver to collect cooled and the condensed liquid mass after condensing the reacted vapors, distillation apparatus to separate the methanol & water from above mixture for recycling of un-reacted methanol, a thin-film evaporator to recover the Guaiacol & Veratrole as a mixture cut was removed from the product mass from the high boiling cut of catechol left in the Thin Film evaporator and recycling the catechol, and a fractional distillation set for the separation of Guaiacol & Veratrole under Vacuum.

DETAILED DESCRIPTION OF THE INVENTION

Process and apparatus of this invention comprise simpler apparatus and easier to operate process and yet gives acceptably good conversion to product.

It is an embodiment of this invention that the vapor mixture generation with desired mix of the diphenol or diphenol derivative and aliphatic and alicyclic alcohols is achieved using a pre-heater (A) and Super-heater (B). It is a further embodiment of this invention that Jacketed section (C) is used to separate and discard the small amount of tar/high boilers that is/are formed. It is also an embodiment of this invention that only the super-heated vapor mixture passes to next reactor to contact the catalyst.

BRIEF DESCRIPTION OF FIGURES AND LEGENDS

FIG. 1: Schematic diagram of process for generating a mixed multi-component vapor for preparation of monoalkyl ethers of diphenols.

A: Pre-heater, B: Super-heater, C: Jacketed section/vessel, D: Catalytic bed, 1: Feed inlet, 2: Vapor mixture, 3: Superheated vapors, 4: Superheated vapor feed to catalytic bed, 5: Product vapors for separation, 6: High boilers to drain, 7: Condensed product vapors to recycle, 8: Hot oil inlet to pre-heater, 9: Hot oil outlet from pre-heater, 10: Hot oil inlet to super-heater, 11: Hot oil outlet from super-heater, 12: Hot oil inlet to jacketed section, 13. Hot oil outlet from jacketed section.

The process scheme consists of mixing a diphenol or diphenol derivative such as catechol, Hydroquinone, Resorcinol, 4-Methyl catechol, 4-Chloro catechol etc. with aliphatic and alicyclic alcohols such as Methanol, ethanol, Isopropyl alcohol, Isobutyl alcohol, tert-butyl alcohol, Cyclohexanol etc. in a mixing vessel at about 40 to 100 deg C. The mixed multi component liquid is then pumped into feed tank via in-line filter so as to separate any un-dissolved component. The clear multi component liquid in feed tank is analyzed & adjusted to desired composition by addition of required component. Preferred composition of the multicomponent liquid comprises one part diphenol or diphenol derivative & 4 parts aliphatic & alicyclic alcohol. The said liquid is then transferred to pre-heater (A) and heated to a temperature of about 265 deg C. to get a vapor that is a multicomponent mixture comprising diphenol/diphenol-derivative, aliphatic & alicyclic alcohol. The rate of introduction of the multicomponent liquid into the pre-heater (A) and temperature of the oil circulating through the jacket of the pre-heater are so set that only the multicomponent vapor that is formed in the pre-heater passes to the section of the super-heater (B). This multi-component vapor is further super-heated to a temperature of 285 deg C. by super-heater (B) heated by a heating source to get the superheated mixed multi component vapors which is delivered at the top of the Jacketed section/vessel (C). At the same time if some of the high boilers escape the process of super heating and condense at the top of the jacketed Vessel (C) a part of it would again vaporize due to heated jacket of (C); and whatever negligible quantity of condensed high boilers that do not vaporize again from the jacket of (C) and the tars that are formed during heating process are removed from the bottom as shown in the figure via "High Boilers to drain" (6) so that only vapors are allowed to pass to next stage. The jacket of (C) is heated by a heating source. The heating source may be hot oil which flows in the jacket through the inlet (12) and comes out through the outlet (13). Temperature of the hot oil is set such that most of the condensed high boilers evaporate again.

The superheated mixed multi component vapors are allowed to pass from the top of the vertical externally heated (jacketed) section (c) through which a heating source circulates. The mixed multi component vapors are ensured to have same composition as that of the multi-component liquid and the super-heated multi-component vapor is then transferred further to the vapor phase catalytic reactor (D).

The non evaporated portion of the mixed multi component liquid is drained from the bottom of the heated section (6).

The catalyst system used & further manufacturing process used for monoalkyl ether synthesis is as mentioned in WO 01/74485 A1 and the method of its preparation followed here has been described in description of the example below. Of course, in place of the catalysts described below, any other catalyst made by any other method that results in catalyzing a reaction between vapors of diphenol or diphenol derivative and aliphatic and alicyclic alcohols to make monoalkyl ethers of diphenols can be substituted.

The catalyst used for this process, designated as ALPO catalyst, consists of Mixed oxides of elements such as Phosphorous & Aluminum and is prepared as mentioned in WO 01/74485 A1. In the illustrative process, the Aluminium/Phosphorus catalyst is prepared by a process comprising following steps: dissolving $AlCl_3.6H_2O$ in 0.5N HCl with stirring, adding 85% $H_3PO_4$ to make a clear solution, adding conc. $NH_4OH$ drop-wise to adjust pH to about 7 to get a precipitate, drying the precipitate to make a paste, drying the paste further to obtain dry white mass, treating the dried mass in air stream at high temperature, subjecting the solid to compression, granulation & sieving to obtain granules containing the Aluminum/Phosphorus analytic ratio in the final catalyst as 0.064±0.04, forming the catalyst into square shapes, mixing the catalyst with binder and Polyvinyl Acetate (PVA) Powder in a kneader, slowly adding distilled water & continuing kneading of the mass so as to form a dough of a consistency similar to that required for bread making, pressing the dough to convert it in noodles shape, slowly drying these noodles until constant weight is achieved, grinding these noodles & passing through a sieve so as to convert it in fine powder, passing the powder through tabletting/pelleting machine so as to convert it in square shape, calcining the square shaped catalyst in Nitrogen atmosphere before using it for reaction. Details are given in the examples described below.

This invention may also be used for developing multi-component vapor mixture for reacting with each other in a catalytic reaction for preparation of producing a monoalkyl ether of a dihydric phenolic compound; the components of the vapor mixture comprising high boiler aromatic compounds having one or more hydroxyl group including, without limitation, phenol, guaiacol, catechol, hydroquinone, resorcinol, 2-methyl catechol, 4-methyl catechol, 2-methyl hydroquinone, 2-chlorocatechol and 4-chlorocatechol; and low boiling organic compounds, which, upon reacting in a vapor state in presence of a catalyst with diphenols, or diphenol derivatives, produces a monoalkyl ether of a dihydric phenolic compound, the organic compound including, without limitation, aliphatic alcohols, cycloaliphatic alcohols, aliphatic ethers, aliphatic ketones, aliphatic glycols, aliphatic carboxylic acid esters, aliphatic hydrocarbons, cycloaliphatic hydrocarbons, aromatic hydrocarbons and water, each having a boiling temperature of 50 to 200. degree. C.

In one embodiment of the invention, the process of this invention comprising steps described below. A diphenol or diphenol derivative is mixed with an aliphatic or alicyclic alcohol. The aliphatic or alicyclic alcohol may comprise, without limitation, Methanol, ethanol, Isopropyl alcohol, Isobutyl alcohol, tert-butyl alcohol, n-butyl alcohol, isoamyl alcohol, Amyl alcohol, 2-Methyl butan-1-ol, Neopentyl alcohol,3-pentanol, Methyl propyl carbinol, Methyl propyl isocarbinol, Tertiary amyl alcohol, cyclohexanol, cyclopentanol, cyclobutanol, and cyclopropanol. The reactants may be taken in a mixing vessel at about 40 to 100 deg C., un-dissolved components filtered out, the clear multi component liquid in feed tank analyzed and the same is adjusted to the desired composition by addition of required component, The multi-component liquid is transferred to pre-heater (A) and super-heater (B) which are heated by a heating source to get the superheated mixed multi component vapors from top of the Jacketed vessel (C). If some of the high boilers escape the process of super heating and condense, they are removed from the bottom of the jacketed vessel via "High Boilers to drain" so that only vapors are allowed to pass to next stage allowing the superheated mixed multi component vapors to pass through a vertical externally heated (jacketed) section (c) through which hot oil goes in through the inlet (12) and comes out through outlet (13), heating the heated section to ensure the complete evaporation of the high boiling component of the mixed multi component liquid, ensuring that the mixed multi component vapors have same composition as that of the multi-component liquid. The non evaporated portion of the mixed multi component liquid is drained off from the bottom of the heated section (6), In particular example of working of this invention, catechol and methanol are charged to a Stainless Steel reactor of 4000 L capacity. The ratio between catechol and methanol may range between 1:20 moles to 1:2 moles. This ratio may more preferably be 1:5 moles. The mixing is done at room temperature under Nitrogen atmosphere. Heating is started to raise the temperature to about 50-70° C. until a clear hot solution of catechol in methanol is formed, the hot solution of Catechol in Methanol is passed through a pre-heater & a super-heater so as to get a multicomponent vapor mixture containing catechol and methanol, which is collected from the jacketed column (C) and fed at the rate of 250 L to 300 L/hr through the tubular reactor catalyst bed (D). The rate of passage of the multicomponent mixture may vary depending on the dimensions of various equipment in this series and also of the number of tubular reactors and their capacities.

The Multiple tubular Reactor used in the illustration contained 146 tubes, each tube having length of 1000 to 1500 cm & diameter 72 cm. These dimensions may be varied as needed. The tubes are filled with heterogeneous Aluminum/Phosphorus catalyst. Usually 100 kg-500 kg, of the catalyst is used in cube form of size 2 mm×2 mm prepared as described above and in the example. The tubular reactor/s is/are heated to 240-300° C. by circulating hot oil & kept under Nitrogen atmosphere throughout the course of the reaction, The reaction temperature is maintained within a range of 240-300° C. during this operation so as to keep the reactants in vapor state during the reaction with the catalyst, Thereafter, the vapors are cooled and the condensed liquid mass comprising Guaiacol, Veratrole, Catechol, water and unreacted methanol is collected in a receiver, The methanol and water are removed from above mixture, Methanol is recycled back to step I and water is discarded, The Guaiacol & Veratrole mixture cut is removed from the product mass through use of Thin Film evaporator (TFE) & the high boiling cut of Catechol left in the TFE is recycled.

The separation of Guaiacol & Veratrole may be achieved by fractional distillation. It is convenient to use a 1000 to 1500 cm packed column (d=60-70 cm) & under Vacuum to get Guaiacol having purity of about 99.75-99.85% and Veratrole—0.2-0.3% with a yield of 50-65%, Residual mass consisting of mainly Catechol having purity of 97-99% is sent without any distillation for recycle in the reaction.

The polymeric tars generated through continuous operation are eliminated from bottom of the reactor (8) as high boilers once in every 4 hours operation.

In the following is described an illustrative example of this invention. The example is intended only as an illustration and does not limit the scope of the invention by any means by the specific reactants used and specific reaction conditions used. Variations from this example that are obvious to a person skilled in the art and obvious equivalents are considered to be within the scope of this invention.

Example 1

In a SS (Stainless Steel) reactor 4000 L capacity Catechol & Methanol was charged in a ratio 1:20 to 1:2 moles. The ratio may be 1:10; preferably 1:5 and mixing may be done at room temperature under Nitrogen atmosphere. Heating was started to raise the temperature to about 50-70° C. until a clear solution is formed.

In a Multiple tubular Reactor containing 146 tubes, the tubes were filled with heterogeneous ALPO catalyst (100 kg-500 kg.) in cube form of size 2 mm×2 mm prepared as per example 2 of WO 01/74485 A1 and as described below under title: "Preparation of catalyst".

The length of each tube was 1000 to 1500 cm & diameter 72 cm. This dimension of the tubes is illustrative; and may be varied as per requirement. The tubular reactor was heated to 240-300° C. by circulating hot oil & kept under Nitrogen atmosphere throughout the course of the reaction.

The Catechol+Methanol hot solution (prepared as above) was passed through a pre-heaters & a super-heater as described previously so as to eliminate any material in solid or liquid state. The vapors so formed are collected from (C) & fed at the rate of 250 L to 300 L/hr through the tubular reactor catalyst bed D. Te catalyst was prepared as described further below.

The reaction temperature is maintained within a range of 240-300 deg C. during this operation so as to keep the reactants in vapor state during the reaction with the catalyst.

Thereafter, the vapors are cooled and the condensed liquid mass is then collected in a receiver. The typical content of this solution is as follows: Guaiacol—50-60%, Veratrole—1.2%, Catechol—40-50% along with un-reacted Methanol & water formed in the reaction. The methanol & water was removed from above mixture. Separation of the methanol and water is done in the illustrative example by distillation. Methanol was recycled back to step I and water was discarded.

The Guaiacol & Veratrole Mixture cut was removed from the product mass through use of Thin Film evaporator (TFE) & the high boiling cut of Catechol left in the TFE was recycled.

The separation of Guaiacol & Veratrole was achieved by fractional distillation using 1000 to 1500 cm packed column (d=60-70 cm) & under Vacuum.

Purity of Guaiacol—99.75-99.85% & Veratrole—0.2-0.3%. Yield 50-65%.

Residual mass consisting of mainly Catechol was sent to Step I without any distillation for reaction. Purity of Catechol was 97-99%. The polymeric tars generated through continuous operation was eliminated from bottom of the reactor (8) as high boilers once in every 4 hours operation.

Preparation of Catalyst 59.2 g of $AlCl_3.6H_2O$ were dissolved in 200 ml of 0.5N HCl (190 ml $H_2O$+10 ml of 37% HCl) with stirring. 21 ml of 85% $H_3PO_4$ by weight are subsequently added. To the clear solution was then added drop-wise conc. $NH_4OH$ (about 90 ml) to adjust pH to about 7. The formed precipitate was subsequently dried by suction on a filter to obtain a paste. The paste was then dried in a static dryer at 120° C. for 12 hours to obtain white mass, which was then treated in air stream at high temp, using following time table as follows: from room temp to 300° C. at 10°/min rate, keeping the temp of 300° C. for 4 hours, subsequent heating from 300 to 600° C. at 10°/min rate, keeping the temp. of 600° C. for 4 hours. The surface area of the resulting sample was 74±5 $m^2/g$. The solid was then subjected to compression, granulation & sieving to obtain granules having average size ranging from 0.5 to 1 mm. The Aluminum/Phosphorus analytic ratio in the final catalyst determined by plasma spectrometry, was 0.064±0.04. The catalyst was then extruded into cube shapes of 2 mm×2 mm by using standard methods as mentioned in the literature.

175 gm of this catalyst was mixed with 37.5 gm of binder (Kaolin or Bentonite clay procured from local supplier) & 37.5 gm of Polyvinyl Acetate (PVA) Powder in a sigma kneader. To this mixture was slowly added 210 ml of distilled water & kneading of mass continued so as to form a dough of a consistency similar to that required for bread making. This dough is then pressed in a mill so as to convert it in noodles shape. These noodles were slowly dried in a dryer at 100 deg C. until constant weight is achieved. Total time required for drying is about 8 hours. Weight of dried product—240 gm.

These noodles are then ground & passed through a 100 mesh sieve so as to convert it in fine powder. This powder is then passed through tabletting/pelleting machine so as to convert it in square shape of size 2 mm×2 mm. This square shaped catalyst has good hardness & strength. It is calcined at about 560 deg C. temperature for 4 hours in Nitrogen atmosphere before using it for reaction.

The invention claimed is:

1. A process for developing a multicomponent vapor mixture by heating of solution of reactants comprising one or more of diphenols, or diphenol derivatives, and an organic compound,
    wherein the organic compound is one which upon reacting in a vapor state in presence of a catalyst with diphenols, or diphenol derivatives, produces a monoalkyl ether of a dihydric phenolic compound;
    wherein, the entire solution of reactants is passed through a pre-heater (A) immediately followed by passing through a super-heater (B) (FIG. 1) so as to completely transform into a super-heated multicomponent vapor mixture generation with desired mix of the diphenol or diphenol derivative and an aliphatic or an alicyclic alcohol without the need of thin film evaporator and circulating line, and except for allowing negligible quantity of high boilers which do not re-evaporate upon heating and tars that are formed to be drained out, the vapor mixture is maintained in vapor state in a jacketed vessel (C), which is kept heated by hot oil circulating through the jacket thereby to avoid the production of non-evaporated multicomponent mixture and condensation of a part of the multicomponent vapor mix once it is generated, and the vapor mix is fed to a catalytic reactor to get monoalkyl ether of a dihydric phenolic compound.

2. The process of claim 1 further comprising subjecting the superheated vapor to vapor phase reaction mediated by a catalyst.

3. The process of claim 2 wherein:
    a. the removal of condensed high boilers is achieved in a jacketed vessel which is kept heated by hot oil circulating through the jacket,
    b. the vapor phase catalytic reaction is mediated in a vapor phase catalytic reactor containing an Aluminium/Phosphorus catalyst.

4. The process of claim 3 wherein the Aluminium/Phosphorus catalyst is prepared by a process comprising following steps:
    a. dissolving $AlCl_3.6H_2O$ in 0.5N HCl with stirring,
    b. adding 85% $H_3PO_4$ to make a clear solution,
    c. adding conc. $NH_4OH$ drop-wise to adjust pH to about 7 to get a precipitate,
    d. drying the precipitate to make a paste,
    e. drying the paste further to obtain dry white mass,
    f. treating the dried mass in air stream at high temperature,
    g. subjecting the solid to compression, granulation & sieving to obtain granules containing the Aluminum/Phosphorus analytic ratio in the final catalyst as 0.064±0.04,
    h. forming the catalyst into square shapes,
    i. mixing the catalyst with binder and Polyvinyl Acetate (PVA) Powder in a kneader,
    j. slowly adding distilled water & continuing kneading of the mass so as to form a dough of a consistency similar to that required for bread making, k. pressing the dough to convert it in noodles shape,
l. slowly drying these noodles until constant weight is achieved,
m. grinding these noodles & passing through a sieve so as to convert it in fine powder,
n. passing the powder through tabletting/pelleting machine so as to convert it in square shape,
o. calcining the square shaped catalyst in Nitrogen atmosphere before using it for reaction.

5. The process of claim 4 wherein:
a. $AlCl_3.6H_2O$ dissolved is 59.2 g, in 0.5N HCl is 200 ml,
b. $H_3PO_4$ added is 21 ml,
c. conc. $NH_4OH$ added is about 90 ml,
d. the precipitate is dried by suction on a filter to obtain a paste,
e. further drying the paste is done in a static dryer at 120° C. for 12 hours,
f. the dried mass is treated in air stream using following time table as follows: from room temp to 300° C. at 10°/min rate, keeping the temp of 300° C. for 4 hours, subsequent heating from 300 to 600° C. at 10°/min rate, keeping the temp. of 600° C. for 4 hours. The surface area of the resulting sample was 74±5 $m^2/g$,
g. the granules of the solids having average size ranging from 0.5 to 1 mm and the Al/P analytic ratio in the final catalyst, as determined by plasma spectrometry, is as 0.064±0.04,
h. the dimensions of the square shaped catalyst are 2 mm×2 mm,
i. the catalyst mixed is 175 gm, the binder is Kaolin or Bentonite clay, 37.5 gm, and Polyvinyl Acetate (PVA) powder is 37.5 gm,
j. distilled water added is 210 ml,
k. the noodles are dried in a dryer at 100 deg C., for about 8 hours, the weight of dried product obtained is 240 gm,
l. Sieve for passing the ground noodles is of a 100 mesh size,
m. the size of the square shaped pellet is 2 mm×2 mm,
n. calcining of the square shaped catalyst is done at about 560 deg C. temperature for 4 hours.

6. The process of claim 1 comprising the steps of:
a. mixing a diphenol or diphenol derivative selected from the group consisting of catechol, Hydroquinone, Resorcinol, 4-methyl catechol or 4-Chloro catechol with an aliphatic or alicyclic alcohol selected from the group consisting of Methanol, Ethanol, Isopropyl alcohol, Isobutyl alcohol, tert-butyl alcohol, n-butyl alcohol, isoamyl alcohol, Amyl alcohol, 2-Methyl butan-1-ol, Neopentyl alcohol,3-pentanol, Methyl propyl carbinol, Methyl propyl isocarbinol, Tertiary amyl alcohol, Cyclohexanol, Cyclopentanol, Cyclobutanol, and Cyclopropanol, in a mixing vessel at about 40 to 100 deg C.,
b. filtering out the un-dissolved component,
c. analyzing the clear multicomponent liquid in feed tank & adjusting the same to desired composition by addition of required component,
d. transferring the multicomponent liquid to pre-heater (A) & super-heater (B) heated by a heating source to get the superheated mixed multicomponent vapors from the multicomponent liquid, receiving superheated steam from top of the Jacketed vessel (C),
e. removing, if some of the high boilers escape the process of super heating and condense, from the bottom of the jacketed vessel via "High Boilers to drain" so that only vapors are allowed to pass to next stage,
f. allowing the superheated mixed multicomponent vapors to pass through a vertical externally heated (jacketed) section (c) through which hot oil goes in through the inlet (12) and comes out through outlet (13), heating the heated section to ensure the complete evaporation of the high boiling component of the mixed multicomponent liquid,
g. ensuring that the mixed multicomponent vapors have same composition as that of the multicomponent liquid,
h. draining off the non evaporated portion of the mixed multicomponent liquid from the bottom of the heated section (6), and
i. allowing the multicomponent superheated steam to pass to the vapor phase catalytic reactor (D) from the top end of the Jacketed Vessel (C) to pass to the vapor phase catalytic reactor (D).

7. The process of claim 6 wherein:
a. catechol and methanol are charged to a Stainless Steel reactor of 4000 L capacity Catechol & Methanol in a ratio ranging between 1:20 moles to 1:2, at room temperature under Nitrogen atmosphere,
b. heating is started to raise the temperature to about 50-70° C. until a clear hot solution of catechol in methanol is formed,
c. in a Multiple tubular Reactor containing 146 tubes, each tube having length of 1000 to 1500 cm & diameter 72 cm, the tubes are filled with heterogeneous Aluminum/Phosphorus catalyst, 100 kg-500 kg, in cube form of size 2 mm×2 mm prepared as per claim 5,
d. the tubular reactor is heated to 240-300° C. by circulating hot oil & kept under Nitrogen atmosphere throughout the course of the reaction,
e. the hot solution of Catechol in Methanol is passed through a pre-heater and a super-heater so as to get a multicomponent vapor mixture containing catechol and methanol, which is collected from the jacketed column (C) and fed at the rate of 250 L to 300 L/hr through the tubular reactor catalyst bed (D),
f. the catalyst was prepared as described in claim 5,
g. the reaction temperature is maintained within a range of 240-300° C. during this operation so as to keep the reactants in vapor state during the reaction with the catalyst,
h. thereafter, the vapors are cooled and the condensed liquid mass comprising Guaiacol, Veratrole, Catechol, water and unreacted methanol is collected in a receiver,
i. the methanol and water are removed from above mixture, Methanol is recycled back to step I and water is discarded,
j. the Guaiacol & Veratrole mixture cut is removed from the product mass through use of Thin Film evaporator (TFE) & the high boiling cut of Catechol left in the TFE is recycled,
k. the separation of Guaiacol & Veratrole is achieved by fractional distillation using 1000 to 1500 cm packed column (d=60-70 cm) & under Vacuum to get Guaiacol having purity of about 99.75-99.85% and Veratrole 0.2-0.3% with a yield of 50-65%,
l. residual mass consisting of mainly Catechol having purity of 97-99% is sent without any distillation for reaction to Step a. of this claim,
m. the polymeric tars generated through continuous operation is eliminated from bottom of the reactor (8) as high boilers once in every 4 hours operation.

8. The process of claim 7, wherein the ratio of catechol and methanol is selected to be at 1:5 moles.

\* \* \* \* \*